(12) United States Patent
Fritz et al.

(10) Patent No.: US 6,995,134 B2
(45) Date of Patent: Feb. 7, 2006

(54) USE OF YNES, ESSENTIAL BACTERIAL GENES AND POLYPEPTIDES

(75) Inventors: Christian Fritz, Natick, MA (US); Philip Youngman, Boston, MA (US); Luz-Maria Guzman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 370 days.

(21) Appl. No.: 10/068,080

(22) Filed: Feb. 5, 2002

(65) Prior Publication Data

US 2002/0115591 A1 Aug. 22, 2002

Related U.S. Application Data

(62) Division of application No. 09/163,445, filed on Sep. 30, 1998, now Pat. No. 6,472,377.
(60) Provisional application No. 60/070,116, filed on Dec. 31, 1997.

(51) Int. Cl.
- *A01N 37/18* (2006.01)
- *A61K 38/00* (2006.01)
- *A61K 31/70* (2006.01)
- *C12Q 1/68* (2006.01)
- *C12Q 1/18* (2006.01)

(52) U.S. Cl. ............... 514/2; 514/12; 514/44; 435/6; 435/32; 435/252.3; 435/253.4

(58) Field of Classification Search ............... 514/2, 514/12, 44; 435/6, 32, 252.3, 253.4
See application file for complete search history.

(56) References Cited

U.S. PATENT DOCUMENTS

| | | | | | |
|---|---|---|---|---|---|
| 3,681,493 | A | * | 8/1972 | Davies | 424/185 |
| 3,927,210 | A | * | 12/1975 | Stapley et al. | 424/118 |
| 4,311,693 | A | * | 1/1982 | Hernandez et al. | 424/122 |
| 4,576,938 | A | * | 3/1986 | Wagatsuma et al. | 514/206 |
| 4,670,466 | A | * | 6/1987 | Chaiet et al. | 101/20 |
| 4,963,569 | A | * | 10/1990 | Currie et al. | 514/326 |

FOREIGN PATENT DOCUMENTS

WO   WO 99/33871   7/1999

OTHER PUBLICATIONS

Chemical Abstract, vol. 128, No. 13, Mar. 30, 1998, Columbus, Ohio, US; abstract No. 150233; XP002128453 abstract.

Fisher et al., "Cloning and Characterization of the *parC* and *parE* Gene of *Streptococcus pneumoniae* Encoding DNA Topoisomerase IV: Role in Fluoroquinolone Resistance," *J. Bacteriol.* 178(14):4060–4069, 1996.

Kunst et al., "The Complete Genome Sequence of the Gram-Positive Bacterium Bacillus Subtilis", *Nature* 390(6657):249–256, 1997.

* cited by examiner

*Primary Examiner*—Rodney P Swartz
*Assistant Examiner*—Khatol S Shahnan-Shah
(74) *Attorney, Agent, or Firm*—Fish & Richardson P.C.

(57) ABSTRACT

Disclosed is a gene, termed "S-yneS," found in *Streptococcus pneumoniae*, which is essential for survival for a wide range of bacteria. This gene and the S-yneS polypeptide that it encodes, as well as homologs and orthologs thereof (collectively referred to as "yneS" genes and polypeptides) can be used to identify antibacterial agents for treating a broad spectrum of bacterial infections.

12 Claims, 4 Drawing Sheets

USE OF YNES, ESSENTIAL BACTERIAL GENES AND POLYPEPTIDES

CROSS-REFERENCE TO RELATED APPLICATION

This application is a divisional of U.S. patent application Ser. No. 09/163,445, filed on Sep. 30, 1998 (now U.S. Pat. No. 6,472,377), which claims priority from U.S. Provisional Application Ser. No. 60/070,116, filed on Dec. 31, 1997, both of which are incorporated herein by reference in their entirety.

FIELD OF THE INVENTION

The invention relates to the use of yneS, an essential bacterial gene, in identifying antibacterial agents.

BACKGROUND OF THE INVENTION

Bacterial infections may be cutaneous, subcutaneous, or systemic. Opportunistic bacterial infections proliferate, especially in patients afflicted with AIDS or other diseases that compromise the immune system. Most bacteria that are pathogenic to humans are gram positive bacteria. The bacterium *Streptococcus pneumoniae*, for example, typically infects the respiratory tract and can cause lobar pneumonia, as well as meningitis, sinusitis, and other infections.

SUMMARY OF THE INVENTION

The invention is based on the discovery that the yneS gene of the gram positive bacterium *Streptococcus pneumoniae*, termed "S-yneS," and of *Bacillus subtilus*, termed "B-yneS," are essential for survival. The terms "yneS gene" and "yneS polypeptide" refer to the S-yneS and B-yneS genes, as well as their homologs and orthologs, collectively. While "homologs" are structurally similar genes contained within a species, "orthologs" are functionally equivalent genes from other species (within or outside of a given genus). The yneS gene is considered an "essential" gene, and the yneS polypeptide is considered an "essential" polypeptide. A yneS gene and polypeptide can be used in methods for identifying similar genes in pathogenic and non-pathogenic microorganisms. A yneS polypeptide can be used to identify compounds that are inhibitors of the pathogens in which the yneS polypeptide is expressed. Such inhibitors attenuate bacterial growth by inhibiting the activity of a yneS polypeptide, or by inhibiting transcription of a yneS gene or translation of the mRNA transcribed from the yneS gene.

The amino acid and nucleic acid sequences of S-yneS are set forth in FIG. 1 as SEQ ID NOs:1 and 2, respectively. The amino acid and nucleic acid sequences of B-yneS are set forth in FIG. 2 as SEQ ID NOs:3 and 4, respectively.

Now that the yneS gene has been identified and shown to be essential for survival, the yneS gene and polypeptide (including homologs and orthologs of the sequences disclosed herein) can be used to identify antibacterial agents. Such antibacterial agents can readily be identified with high throughput assays to detect inhibition of the metabolic pathway in which the yneS polypeptide participates. This inhibition can be caused by small molecules interacting with (e.g., binding directly or indirectly to) the yneS polypeptide or other essential polypeptides in that pathway.

In an exemplary assay, but not the only assay, a promoter that responds to depletion of the essential yneS polypeptide by upregulation or downregulation is linked to a reporter gene. To identify a promoter that is up- or down-regulated by the depletion of a yneS protein, the gene encoding the yneS protein is deleted from the genome and replaced with a version of the gene in which the sequence encoding the yneS protein is operably linked to a regulatable promoter. The cells containing this regulatable genetic construct are kept alive by the essential yneS polypeptide produced from the genetic construct containing the regulatable promoter. However, the regulatable promoter allows the expression of the yneS polypeptide to be reduced to a level that causes growth inhibition. Total RNA prepared from bacteria under such growth-limiting conditions is compared with RNA from wild-type cells. Standard methods of transcriptional profiling can be used to identify mRNA species that are either more or less abundant (i.e., up- or down-regulated) when expressed under the limiting conditions. Genomic sequence information, e.g., from GenBank, can be used to identify a promoter that drives expression of the identified RNA species. Such promoters are up- or down-regulated by depletion of the yneS polypeptide.

Having identified a promoter(s) that is up- or down-regulated by depletion of the yneS polypeptide, the promoter (s) is operably linked to a reporter gene (e.g., β-galactosidase, gus, or green fluorescent protein (GFP)). A bacterial strain containing this reporter gene construct is then exposed to test compounds. Compounds that inhibit the yneS polypeptide (or other polypeptides in the essential pathway in which the yneS polypeptide participates) will cause a functional depletion of the yneS polypeptide and therefore lead to an upregulation or downregulation of expression of the reporter gene. Because the polypeptides described herein are essential for the survival of bacteria, compounds that inhibit the yneS polypeptides in such an assay are expected to be antibacterial and can be further tested, if desired, in standard susceptibility assays.

Another suitable method for identifying antibacterial compounds involves screening for small molecules that specifically interact with (i.e., bind directly or indirectly to) the essential yneS polypeptide. A variety of suitable interaction and binding assays are known in the art as described, for example, in U.S. Pat. Nos. 5,585,277 and 5,679,582, incorporated herein by reference. For example, in various conventional assays, test compounds can be assayed for their ability to interact with a yneS polypeptide by measuring the ability of the small molecule to stabilize the yneS polypeptide in its folded, rather than unfolded, state. More specifically, one can measure the degree of protection against unfolding that is afforded by the test compound. Test compounds that bind the yneS polypeptide with high affinity cause, for example, a large shift in the temperature at which the polypeptide is denatured. Test compounds that stabilize the yneS polypeptide in a folded state can be further tested for antibacterial activity in a standard susceptibility assay.

In a related method for identifying antibacterial compounds, the essential yneS polypeptide is used to isolate peptide or nucleic acid ligands that specifically bind the yneS polypeptide. These peptide or nucleic acid ligands are then used in a displacement screen to identify small molecules that interact with the yneS polypeptide. Such assays can be carried out essentially as described above.

Another suitable method for identifying inhibitors of the essential yneS polypeptide involves identifying a biochemical activity of the polypeptide and then screening for small molecule inhibitors of the activity using, for example, a high throughput screening method.

The various yneS polypeptides can be used, separately or together, in assays to identify test compounds that interact with these polypeptides. Test compounds that interact with these polypeptides then can readily be tested, in conventional assays, for their ability to inhibit bacterial growth. Test compounds that interact with the yneS polypeptides are candidate antibacterial agents, in contrast to compounds that do not interact with the yneS polypeptides. As described herein, any of a variety of art-known methods can be used to assay for the interaction of test compounds with the yneS polypeptides.

The invention also includes a method for identifying an antibacterial agent where the method entails: (a) contacting an essential yneS polypeptide with a test compound; (b) detecting binding of the test compound to the polypeptide; and, optionally, (c) determining whether a test compound that binds to the yneS polypeptide inhibits growth of bacteria, relative to growth of bacteria cultured in the absence of the test compound that binds to the yneS polyepeptide, as an indication that the test compound is an antibacterial agent.

In still another method, interaction of a test compound with a yneS polypeptide (e.g., binding) can be detected in a conventional two-hybrid system for detecting protein/protein interactions (e.g., in yeast or mammalian cells). A test compound found to interact with the yneS polypeptide can be further tested for antibacterial activity in a conventional susceptibility assay. Generally, in such two-hybrid methods, (a) the yneS polypeptide is provided as a fusion protein that includes the polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the polypeptide is detected as a reconstitution of a transcription factor. Homologs and orthologs of S-yneS and B-yneS polypeptide described herein can be used in such methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding a yneS polypeptide is used to identify a compound that decreases the expression of a yneS polypeptide in vivo (i.e., in a cell). Such compounds can be used as antibacterial agents. To discover such compounds, cells that express a yneS polypeptide are cultured, exposed to a test compound (or a mixture of test compounds), and the level of expression or activity is compared with the level of yneS polypeptide expression or activity in cells that are otherwise identical but that have not been exposed to the test compound(s). Many standard quantitative assays of gene expression can be utilized in this aspect of the invention.

To identify compounds that modulate expression of a yneS polypeptide, the test compound(s) can be added at varying concentrations to the culture medium of cells that express a yneS polypeptide, as described herein. Such test compounds can include small molecules (typically, non-protein, non-polysaccharide chemical entities), polypeptides, and nucleic acids. The expression of the yneS polypeptide is then measured, for example, by Northern blot PCR analysis or RNAse protection analyses using a nucleic acid molecule described herein as a probe. The level of expression in the presence of the test molecule, compared with the level of expression in its absence, will indicate whether or not the test molecule alters the expression of the yneS polypeptide. Because the yneS polypeptides (including homologs and orthologs of the sequences disclosed herein) are essential for survival, test compounds that inhibit the expression and/or function of the yneS polypeptide will inhibit growth of, or kill, the cells that express such yneS polypeptides.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, and the like can be screened to identify compounds that bind the yneS polypeptide. More generally, binding of test a compound to the yneS polypeptide can be detected either in vitro or in vivo. If desired, the above-described methods for identifying compounds that modulate the expression of yneS polypeptides can be combined with measuring the levels of the yneS polypeptides expressed in the cells, e.g., by performing a Western blot analysis using antibodies that bind a yneS polypeptide.

Regardless of the source of the test compound, the yneS polypeptides described herein can be used to identify compounds that inhibit the activity of a yneS protein or transcription of a yneS gene or translation of the mRNA transcribed from the yneS gene. These antibacterial agents can be used to inhibit a wide spectrum of pathogenic or non-pathogenic bacterial strains, particularly gram-positive bacteria.

In other embodiments, the invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic bacterial strains (e.g., pathogenic gram positive bacterial strains such as pathogenic *Streptococcus* strains). Such pharmaceutical formulations can be used in a method of treating a bacterial infection in an organism (e.g., a *Streptococcus* infection). Such a method entails administering to the organism a therapeutically effective amount of the pharmaceutical formulation, i.e., an amount sufficient to ameliorate signs and/or symptoms of the bacterial infection. In particular, such pharmaceutical formulations can be used to treat bacterial infections in mammals such as humans and domesticated mammals (e.g., cows, pigs, dogs, and cats), and in plants. The efficacy of such antibacterial agents in humans can be estimated in an animal model system well known to those of skill in the art (e.g., mouse and rabbit model systems of, for example, *streptococcal pneumonia*).

Various affinity reagents that are permeable to the microbial membrane (i.e., antibodies and antibody fragments) are useful in practicing the methods of the invention. For example polyclonal and monoclonal antibodies that specifically bind to the yneS polypeptide can facilitate detection of yneS polypeptides in various bacterial strains (or extracts thereof). These antibodies also are useful for detecting binding of a test compound to yneS polypeptides (e.g., using the assays described herein). In addition, monoclonal antibodies that bind yneS polypeptides can themselves be used as antibacterial agents.

The invention further features methods of identifying from a large group of mutant strains those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of antibacterial therapeutic agents. These antibacterial agents reduce the action of the gene product in a wild type strain, and therefore are useful in treating a subject with that type, or a similarly susceptible type, of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic bacterium of the same genus or similar species), and the absence or divergence of the sequence in host cells can be determined, if desired. Therapeutic agents directed toward genes or gene products that are not present in the host have several advantages, including fewer side effects, and lower overall dosage.

In various embodiments, the yneS polypeptide used in the assays described herein is derived from a non-pathogenic or pathogenic gram positive bacterium. For example, a yneS polypeptide can be derived from a *Streptococcus* strain, such as *Streptococcus pneumoniae, Streptococcus pyogenes, Streptococcus agalactiae, Streptococcus endocarditis, Streptococcus faecium, Streptococcus sangus, Streptococcus viridans,* and *Streptococcus hemolyticus.* Suitable orthologs of the S-yneS gene can be derived from a wide spectrum of bacteria, such as *Bacillus subtilis* and *E. coli.*

The invention offers several advantages. For example, the methods for identifying antibacterial agents can be configured for high throughput screening of numerous candidate antibacterial agents. Because the essential yneS gene disclosed herein is thought to be highly conserved, antibacterial drugs targeted to this gene or its gene products are expected to have a broad spectrum of antibacterial activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIG. 1 is a listing of the amino acid and nucleic acid sequences of a yneS polypeptide and gene from a *Streptococcus pneumoniae* strain (SEQ ID NOs:1 and 2, respectively). The complement of the nucleic acid sequence is set forth as SEQ ID NO:11.

FIG. 2 is a listing of the full-length amino acid and nucleic acid sequences of a yneS polypeptide and gene from a *B. subtilis* strain (SEQ ID NOs:3 and 4, respectively). The complement of the nucleic acid sequence is set forth as SEQ ID NO: 12.

DETAILED DESCRIPTION OF THE INVENTION

Figure 3:
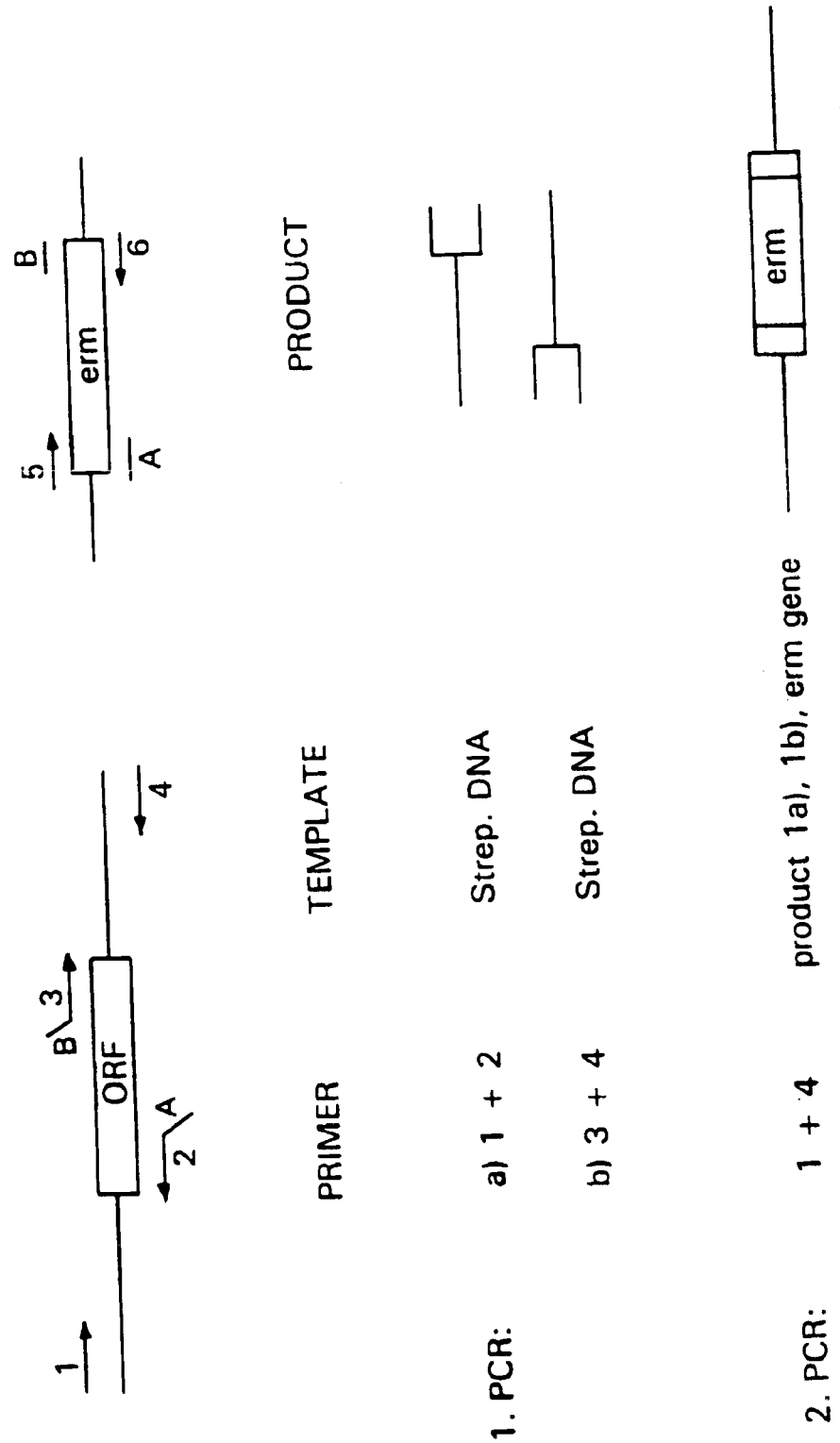
FIG. 3 is a schematic representation of the PCR strategy used to produce DNA molecules used for targeted deletions of essential genes in *Streptococcus pneumoniae.*

A gene in the bacterium *Streptococcus pneumoniae* has been found to be essential for the survival of this bacterium. This so-called essential gene, S-yneS, encodes what is referred to herein as a S-yneS polypeptide. The S-yneS gene can be used to identify similar genes in pathogenic microorganisms, such as pathogenic gram-positive bacteria (e.g., *Bacillus*). A yneS gene from *Bacillus subtilis*, termed B-yneS, has been found to be essential for survival. These yneS polypeptides can be used in methods for identifying compounds that are inhibitors of the pathogens in which yneS polypeptides are expressed (e.g., pathogenic and non-pathogenic bacteria, and gram-positive bacteria in particular).

Nucleic acids used in practicing the methods of the invention include both RNA and DNA, including genomic DNA and synthetic (e.g., chemically synthesized) DNA. Nucleic acids can be double-stranded or single-stranded. Where single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

Figure 1:
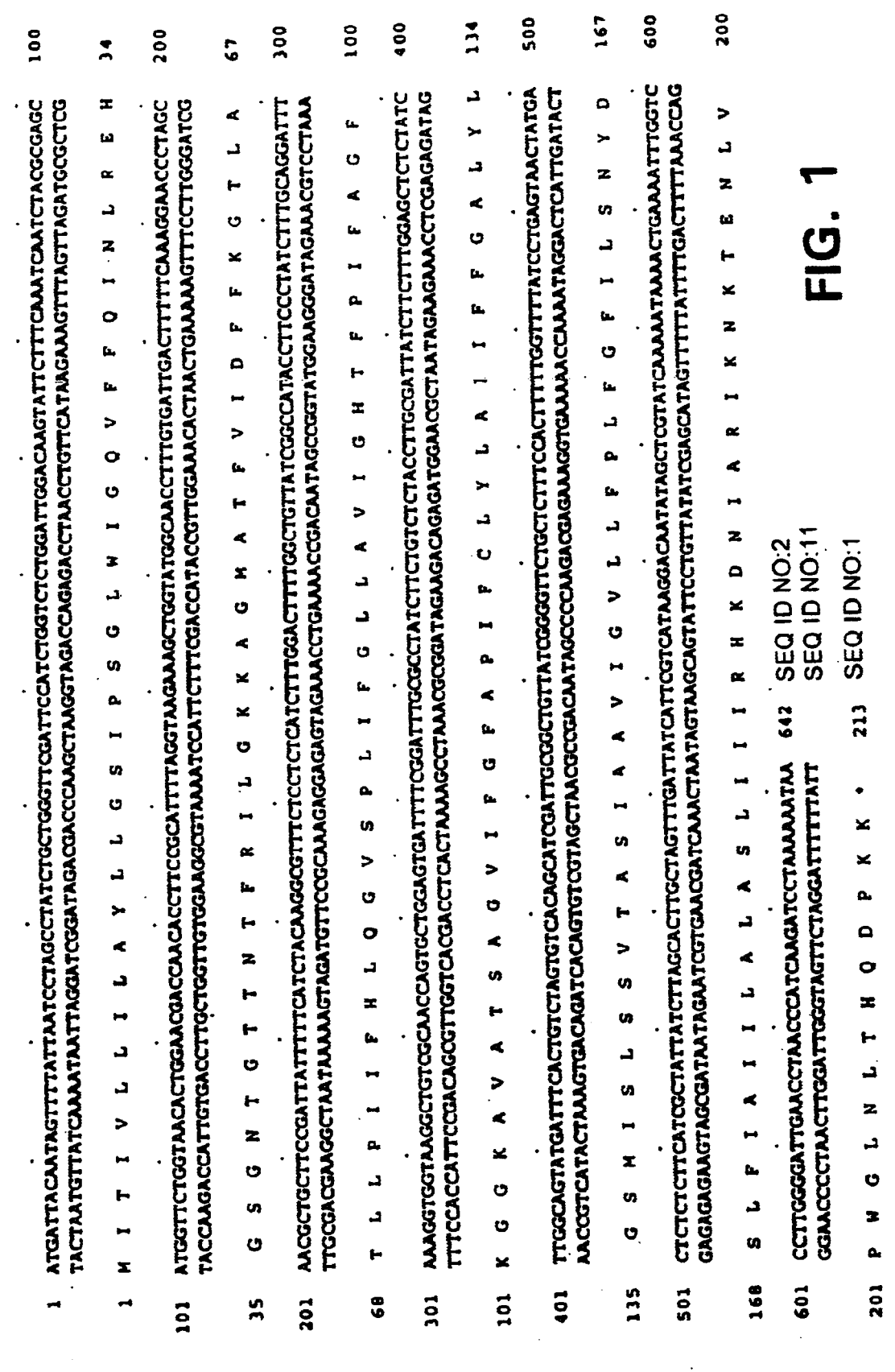
Figure 2:
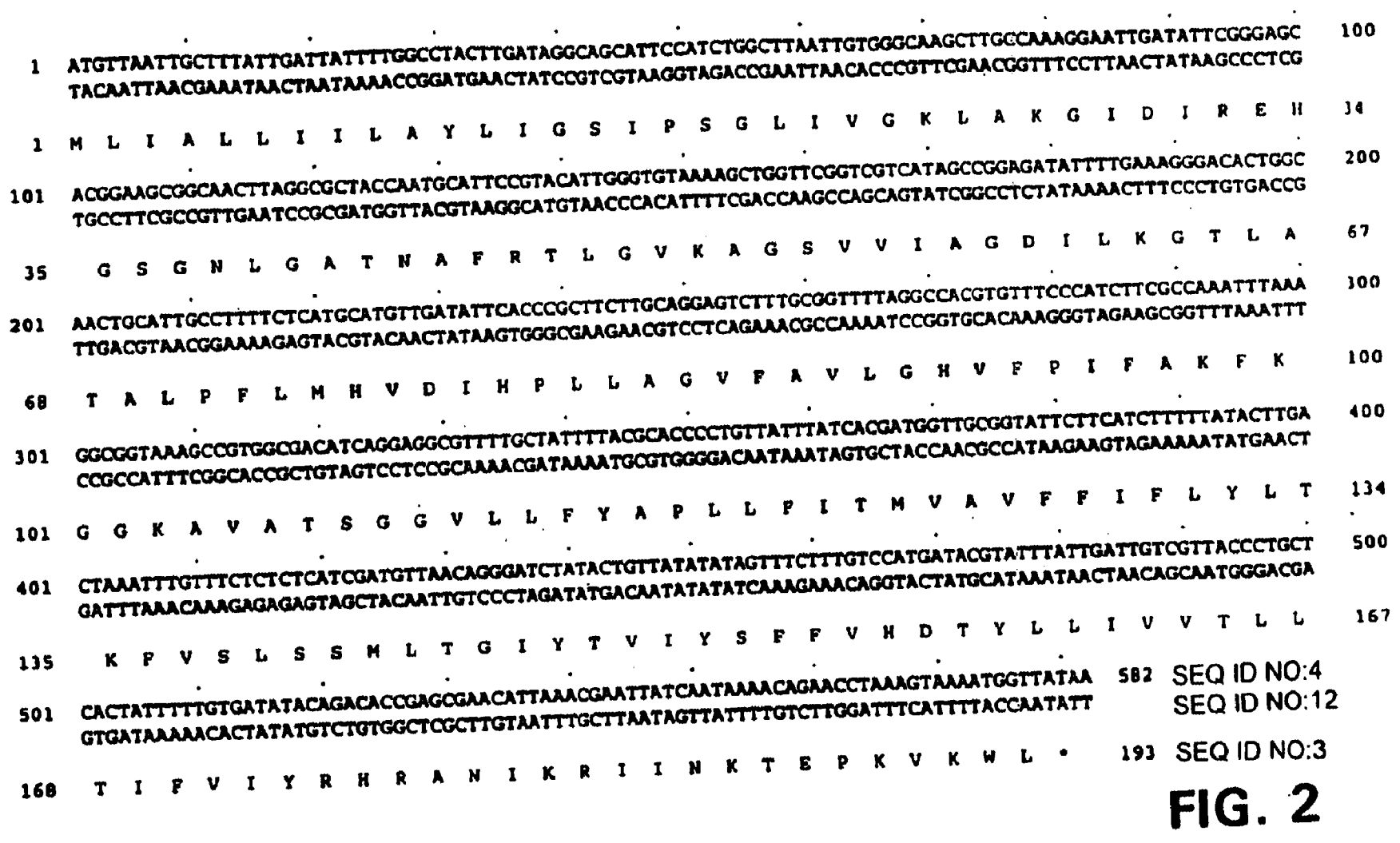

A nucleic acid sequence that is substantially identical to an S-yneS or B-yneS nucleotide sequence is at least 80% identical to the nucleotide sequence represented by SEQ ID NO:2, as depicted in FIG. 1 or SEQ ID NO:4, as depicted in FIG. 2, respectively. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A suitable, mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to yneS nucleic acid molecules described herein. BLAST protein searches can be performed with the XBLAST program, score=50, wordlength=3 to obtain amino acid sequences homologous to yneS protein molecules. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See the National Institute of Health website at address: World Wide Web (www) ncbi.nlm.nih.gov Another example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The yneS polypeptides useful in practicing the invention include, but are not limited to, recombinant polypeptides and natural polypeptides. Also useful in the invention are nucleic acid sequences that encode forms of yneS polypeptides in which naturally occurring amino acid sequences are altered or deleted. Preferred nucleic acids encode polypeptides that are soluble under normal physiological conditions. Also useful are nucleic acids encoding fusion proteins in which a portion of a yneS polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. Also useful in practicing the methods of the invention are isolated polypeptides (and the nucleic acids that encode these polypeptides) that include a first portion and a second portion; the first portion includes, e.g., a yneS polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Additional useful nucleic acids include nucleic acids that encode a yneS polypeptide fused to a polypeptide sequence to produce an inactive preprotein. Preproteins can be converted into the active form of the protein by removal of the inactivating sequence.

Nucleic acids that hybridize, e.g., under moderate or highly stringent hybridization conditions (as defined herein) to all or a portion of the nucleotide sequences represented by SEQ ID NOs:2 or 4, or their complements, can be used to identify additional homologs or orthologs of S-yneS and B-yneS. The hybridizing portion of the hybridizing nucleic acids is typically at least 15 (e.g., 20, 25, 30, or 50) nucleotides in length. The hybridizing portion of the hybridizing nucleic acid is at least 80%, e.g., at least 95%, or at least 98%, identical to the sequence of a portion or all of a nucleic acid encoding a yneS polypeptide or its complement. Hybridizing nucleic acids of the type described herein can be used as a cloning probe, a primer (e.g., a PCR primer), or a diagnostic probe. Nucleic acids that hybridize to the nucleotide sequences represented by SEQ ID NOs:2 or 4 are considered "antisense oligonucleotides."

Cells that may be used in practicing the methods of the invention include various engineered cells, e.g., transformed host cells, that contain a yneS nucleic acid described herein. A transformed cell is a cell into which (or into an ancestor of which) has been introduced, by means of recombinant DNA techniques, a nucleic acid encoding a yneS polypeptide. Both prokaryotic and eukaryotic cells are included, e.g., bacteria, such as Streptococcus, Bacillus, and the like.

Various genetic constructs (e.g., vectors and plasmids) that include a yneS nucleic acid that is operably linked to a transcription and/or translation sequence to enable expression (e.g., expression vectors) can be used in practicing the methods of the invention. A selected nucleic acid, e.g., a DNA molecule encoding a yneS polypeptide, is "operably linked" to a transcription and/or translation sequence when it is positioned adjacent to one or more sequence elements, e.g., a promoter, which direct transcription and/or translation of the sequence such that the sequence elements can control transcription and/or translation of the selected nucleic acid.

The terms "protein" and "polypeptide" both refer to any chain of amino acids, regardless of length or post-translational modification (e.g., glycosylation or phosphorylation). Thus, the term yneS polypeptide includes full-length, naturally occurring, isolated yneS proteins, as well as recombinantly or synthetically produced polypeptides that correspond to the full-length, naturally occurring protein, or to a portion of the naturally occurring or synthetic polypeptide.

A purified or isolated compound is a composition that is at least 60% by weight the compound of interest, e.g., a yneS polypeptide or antibody. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred yneS polypeptides include a sequence substantially identical to all or a portion of a naturally occurring yneS polypeptide, e.g., including all or a portion of the sequence shown in FIG. 1 or 2. Polypeptides "substantially identical" to the yneS polypeptide sequence described herein have an amino acid sequence that is at least 80% identical to the amino acid sequence of the yneS polypeptide represented by SEQ ID NO:1 or SEQ ID NO:2 (measured as described herein). The new polypeptides can also have a greater percentage identity, e.g., 85%, 90%, 95%, or even higher. For purposes of comparison, the length of the reference yneS polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. Alternatively, it can be a 100 amino acid long polypeptide that is 50% identical to the reference polypeptide over its entire length. Of course, other polypeptides also will meet the same criteria.

The methods of the invention also make use of purified or isolated antibodies that specifically bind to a yneS polypeptide. An antibody "specifically binds" to a particular antigen, e.g., a yneS polypeptide, when it binds to that antigen, but does not substantially recognize and bind to other molecules in a sample, e.g., a biological sample, that naturally includes a yneS polypeptide.

The various nucleic acids described herein can be used in a method of obtaining a gene related to a yneS gene. Such a method entails obtaining a labeled probe that includes an isolated nucleic acid which encodes all or a portion of a yneS nucleic acid, or a homolog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the yneS gene (e.g., homologs and orthologs of yneS).

Identifying the *Streptococcus* S-yneS Gene

As shown by the experiments described below, the S-yneS gene is essential for survival of *Streptococcus pneumoniae*. *Streptococcus pneumoniae* is available from the ATCC. In general, and for the examples set forth below, yneS genes can be identified by creating targeted deletions of genes of interest in a bacterium, e.g., *S. pneumoniae*. The gene of interest was selected as follows. Using standard molecular biology techniques, a library containing fragments of the *Streptococcus pneumoniae* genome was made, using M13 phage or plasmid DNA as the vector. Open reading frames (ORFs) contained within this library were randomly sequenced, using primers that hybridized to the vector. The gene of interest selected for targeted deletion satisfied four criteria, as determined by comparing the sequences with the GenBank database of nucleotide sequences: (i) the ORF had no known function; (ii) the ORF had an ortholog in *Bacillus subtilis*; (iii) the ORF was conserved in other bacteria, with $p<10^{-10}$; and (iv) the ORF had no eukaryotic ortholog, with $p>10^{-3}$. The *Streptococcus* gene S-yneS met each of these criteria, suggesting that a compound that inhibited the S-yneS gene or gene product would have a broad spectrum of antibacterial activity.

The S-yneS gene was replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the *Streptococcus* genomic DNA, as shown in FIG. 3. Several PCR reactions were used to produce the DNA molecules needed to carry out target deletion of the genes of interest. First, using primers 5 and 6, an erm gene was amplified from pIL252 from *B. subtilis* (available from the *Bacillus* Genetic Stock Center, Columbus, Ohio). Primer 5 consists of 21 nucleotides that are identical to the promoter region of the erm gene and complementary to Sequence A. Primer 5 has the sequence 5'GTG TTC GTG CTG ACT TGC ACC3' (SEQ ID NO:5). Primer 6 consists of 21 nucleotides that are complementary to the 3' end of the erm gene. Primer 6 has the sequence 5'GAA TTA TTT CCT CCC GTT AAA3' (SEQ ID NO:6). PCR amplification of the erm gene was carried out under the following conditions: cycles of 94° C. for 1 minute, 55° C. for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 3, this reaction utilized primer 1, which is 21 nucleotides in length and identical to a sequence that is located approximately 500 bp upstream of the translation start site of the gene of interest. Primers 1 and 2 are gene-specific and include the sequences 5'ACC CAC TCC GTG AAG TCC ACC3' (SEQ ID NO:7) and 5'GAA CCC AGC AGA TAG GCT AGG3' 3' (SEQ ID NO:8), respectively, for yneS. Primer 2 is 42 nucleotides in length, with 21 of the nucleotides at the 3' end of the primer being complementary to the 5' end of the sense strand of the gene of interest. The 21 nucleotides at the 5' end of the primer were identical to Sequence A and are therefore complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 3.

The third PCR reaction was similar to the second reaction, but produced the right flanking DNA molecule, shown in FIG. 3. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For S-yneS, primers 3 and 4 included the sequences 5'GAA CCT AAC CCA TCA AGA TCC3' (SEQ ID NO:9) and 5'CAG TTT TAG ATG GCT TTA ACA GCG3' (SEQ ID NO:10), respectively. Primer 3 is 42 nucleotides; the 21 nucleotides at the 5' end of Primer 3 are identical to Sequence B and therefore are identical to the 3' end of the erm gene. The 21 nucleotides at the 3' end of Primer 3 are identical to the 3' end of the gene of interest. Primer 4 is 21 nucleotides in length and is complementary to a sequence located approximately 500 bp downstream of the gene of interest.

PCR amplification of the left and right flanking DNA molecules was carried out, separately, in 50 µl reaction mixtures containing: 1 µl Streptococcus pneumoniae (RX1) DNA (0.25 µg), 2.5 µl Primer 1 or Primer 4 (10 pmol/µl), 2.5 µl Primer 2 or Primer 3 (20 pmol/µl), 1.2 µl a mixture dNTPs (10 mM each), 37 µl H$_2$O, 0.7 µl Taq polymerase (5 U/µl), and 5 µl 10× Taq polymerase buffer (10 mM Tris, 50 mM KCl, 2.5 mM MgCl$_2$). The left and right flanking DNA molecules were amplified using the following PCR cycling program: 95° C. for 2 minutes; 72° C. for 1 minute; 94° C. for 30 seconds; 49° C. for 30 seconds; 72° C. for 1 minute; repeating the 94° C., 49° C., and 72° C. incubations 30 times; 72° C. for 10 minutes and then stopping the reactions. A 15 µl aliquot of each reaction mixture then was electrophoresed through a 1.2% low melting point agarose gel in TAE buffer and then stained with ethidium bromide. Fragments containing the amplified left and right flanking DNA molecules were excised from the gel and purified using the QIAQUICK™ gel extraction kit (Qiagen, Inc.) Other art-known methods for amplifying and isolating DNA can be substituted. The flanking left and right DNA fragments were eluted into 30 µl TE buffer at pH 8.0.

The amplified erm gene and left and right flanking DNA molecules were then fused together to produce the fusion product, as shown in FIG. 3. The fusion PCR reaction was carried out in a volume of 50 µl containing: 2 µl of each of the left and right flanking DNA molecules and the erm gene PCR product; 5 µl of 10× buffer; 2.5 µl of Primer 1 (10 pmol/µl); 2.5 µl of Primer 4 (10 pmol/µl), 1.2 µl DNTP mix (10 mM each) 32 µl H$_2$O, and 0.7 µl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C. and 72° C. incubations 25 times; 72° C. for 10 minutes. After the reaction was stopped, a 12 µl aliquot of the reaction mixture was electrophoresed through an agarose gel to confirm the presence of a final product of approximately 2 kb.

Figure 4:
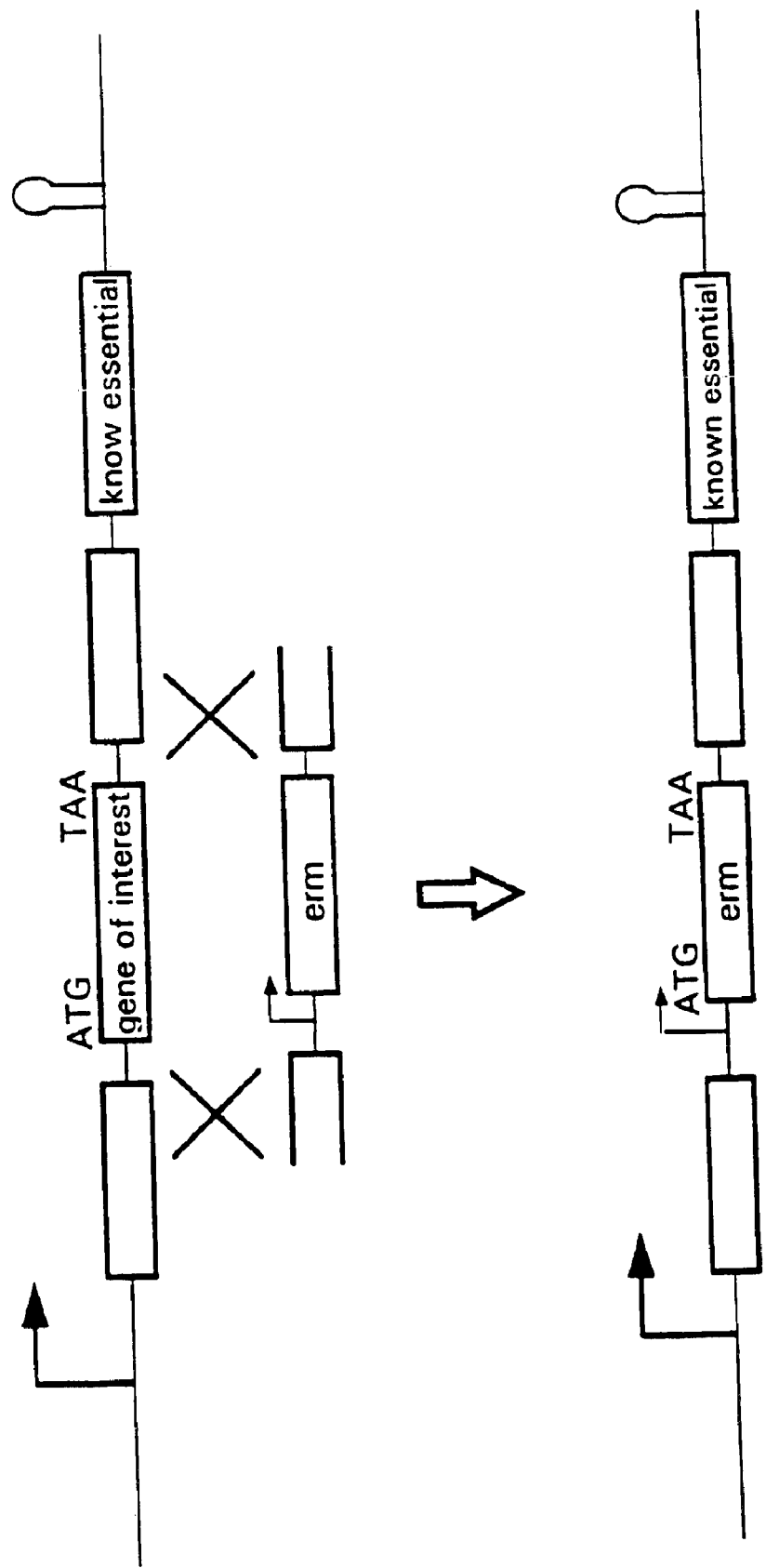
FIG. 4 is a schematic representation of the strategy used to produce targeted deletions of essential genes in *Streptococcus pneumoniae.*

A 5 µl aliquot of the fusion product was used to transform S. pneumoniae grown on a medium containing erythromycin in accordance with standard techniques. As shown in FIG. 4, the fusion product and the S. pneumoniae genome undergo a homologous recombination event so that the erm gene replaces the chromosomal copy of the gene of interest, thereby creating a gene knockout. Disruption of a yneS gene results in no growth on a medium containing erythromycin. Using this gene knockout method, the yneS gene was identified as being essential for survival.

Identification of Homologs and Orthologs of the S-yneS Gene

Having shown that the S-yneS gene is essential for survival of Streptococcus, it can be expected that homologs and orthologs of this gene, when present in other organisms, for example B. subtilis, are essential for survival of those organisms as well. The coding sequences of S-yneS was used to search the GenBank database of nucleotide sequences, and an ortholog of the S-yneS sequence was identified in B. subtilis. Sequence comparisons were performed using the Basic Local Alignment Search Tool (BLAST) (Altschul et al., J. Mol. Biol. 215:403–410, 1990). The percent sequence identity shared by the S-yneS polypeptides and the B. subtilis ortholog, B-yneS, was determined using the GAP program from the Genetics Computer Group (GCG) Wisconsin Sequence Analysis Package (Wisconsin Package Version 9.1; Madison, Wis.). The default parameters for gap weight (12) and length weight (4) were used.

Typically, yneS polypeptides and their homologs or orthologs share at least 25% (e.g., at least 30%, 35%, or 40%) sequence identity. Typically, the DNA sequences encoding yneS polypeptides and their homologs or orthologs share at least 20% (e.g., at least 30%, 35%, 40% or 45%) sequence identity. Bioinformatics analysis of the S-yneS gene showed that this gene is widely conserved among bacteria. To confirm that the identified ortholog of S-yneS, B-yneS, is essential for survival of B. subtilus, the B-yneS gene was deleted from the B. subtilus genome. Such a deletion strain has been constructed and does not survive, confirming the essential nature of the polypeptide. The fact that the B-yneS gene also is essential for survival suggests that yneS genes are essential in all bacteria in which they are present. Therefore, an antibacterial drug targeted to a yneS gene or gene product is expected to have a broad spectrum of antibacterial activity.

Identification of YneS Genes and Polypeptides in Additional Bacterial Strains and Species Now that the S-yneS and B-yneS genes have been identified as being essential for survival, these genes, or fragments thereof, can be used to detect homologous or orthologous genes in yet other organisms. In particular, these genes can be used to analyze various pathogenic and non-pathogenic strains of bacteria, particularly gram-positive bacteria. Fragments of a nucleic acid (DNA or RNA) encoding a yneS polypeptide (including homologs and orthologs of the sequences listed herein, or sequences complementary thereto) can be used as probes in conventional nucleic acid hybridization assays of nucleic acids from bacteria. For example, nucleic acid probes (which typically are 8–30, or usually 15–20, nucleotides in length) can be used to detect yneS genes in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragment thereof, is labeled and used to screen a genomic library constructed from mRNA obtained from a bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to highly stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.50° and 1.5° C. per 1% mismatch.

High stringency hybridization conditions include, for example, hybridizing at 68° C. in 5×SSC/5× Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic bacterial strains can be screened. For example, such strains can be screened for expression of yneS genes by Northern blot analysis. Upon detection of transcripts of a yneS gene, libraries can be constructed from RNA isolated from the appropriate strain, utilizing standard techniques well known to those of skill in the art. Alternatively, a total genomic DNA library can be screened using a yneS gene probe.

New gene sequences can be isolated, for example, by performing PCR using two degenerate oligonucleotide primer pools designed on the basis of nucleotide sequences within the yneS gene (including homologs and orthologs of the sequences disclosed herein), as described herein. The template for the reaction can be DNA obtained from strains known to express, or suspected of expressing, a yneS allele (including alleles of homologs or orthologs of the sequences disclosed herein). The PCR product can be subcloned and sequenced to ensure that the amplified sequences represent the sequences of a new yneS nucleic acid sequence.

Synthesis of a yneS polypeptide can readily be accomplished using any of the various art-known techniques. For example, a yneS polypeptide can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or in insect cells (e.g., by using a baculovirus-based expression vector).

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology,* John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors: A Laboratory Manual* (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, a yneS polypeptide (including homologs and orthologs of the sequences disclosed herein) can be produced as a fusion protein. For example, the expression vector pUR278 (Ruther et al., *EMBO J.,* 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding a yneS polypeptide can be cloned into a non-essential region (for example the polyhedrin gene) of the viral genome and placed under control of a promoter, e.g., the polyhedrin promoter or an exogenous promoter. Successful insertion of a gene encoding a yneS polypeptide can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., *J. Virol.,* 46:584, 1983; Smith, U.S. Pat. No. 4,215,051). If desired, mammalian cells can be used in lieu of insect cells, provided that the virus is engineered such that the gene encoding the desired polypeptide is placed under the control of a promoter that is active in mammalian cells.

In mammalian host cells, a number of viral-based expression systems can be utilized. When an adenovirus is used as an expression vector, the nucleic acid sequence encoding the yneS polypeptide can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a yneS gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., *Methods in Enzymol.,* 153:516, 1987).

YneS polypeptides can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the yneS polypeptide (including homologs and orthologs of the sequences described herein) can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the yneS polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyltransferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, the yneS polypeptide, or a portion thereof, can be fused to an immunoglobulin Fc domain. Such a fusion protein can be readily purified using a protein A column, for example. Moreover, such fusion proteins permit the production of a chimeric form of a yneS polypeptide having increased stability in vivo.

Once the recombinant yneS polypeptide is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-yneS antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate a yneS polypeptide (e.g., a yneS-maltose binding fusion protein, a yneS-$\beta$-galactosidase fusion protein, or a yneS-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of yneS polypeptides, can be produced by standard chemical synthesis (e.g., by the methods described in *Solid Phase Peptide Synthesis*, 2nd ed., The Pierce Chemical Co., Rockford, IL, 1984) and used as antigens, for example.

Assay for Antibacterial Agents

The invention provides methods for identifying antibacterial agent. Although the inventor is not bound by any particular theory as to the biological mechanism involved, the new antibacterial agents are thought to inhibit specifically (1) the function of a yneS polypeptide or (2) expression of a yneS gene. In preferred methods, screening for antibacterial agents is accomplished by identifying those compounds (e.g., small organic molecules) that inhibit the activity of a yneS polypeptide or the expression of a yneS gene.

In an exemplary assay, but not the only assay, a promoter that responds to depletion of the yneS polypeptide by upregulation or downregulation is linked to a reporter gene (e.g., $\beta$-galactosidase, gus, or GFP), as described above. A bacterial strain containing this reporter gene construct is then exposed to test compounds. Compounds that inhibit the yneS polypeptide (or other polypeptides in the essential pathway in which the yneS polypeptide participates) will cause a functional depletion of the yneS polypeptide and therefore lead to an upregulation or downregulation of expression the reporter gene. Because the polypeptides described herein are essential for the survival of bacteria, compounds that inhibit the yneS polypeptides in such an assay are expected to be antibacterial agents and can be further tested, if desired, in conventional susceptibility assays.

In other suitable methods, screening for antibacterial agents is accomplished by (i) identifying those compounds that interact with or bind to a yneS polypeptide and (ii) further testing such compounds for their ability to inhibit bacterial growth in vitro or in vivo.

Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with a yneS polypeptide(s)

by adding the polypeptide(s) in a solution (typically, at a concentration of 0.05 to 1 mg/ml in a volume of 1–100 µl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Interaction of the test compound with yneS polypeptide(s) can be detected by any of a variety of art-known methods. For example, an antibody that specifically binds a yneS polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-YneS antibody). In an alternative detection method, the yneS polypeptide is labeled, and the label is detected (e.g., by labeling a yneS polypeptide with a radioisotope, fluorophore, chromophore, or the like). In still another method, the yneS polypeptide is produced as a fusion protein with a protein that can be detected optically, e.g., green fluorescent protein (which can be detected under UV light). In an alternative method, the polypeptide (e.g., yneS) can be produced as a fusion protein with an enzyme having a detectable enzymatic activity, such as horse radish peroxidase, alkaline phosphatase, β-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various in vivo methods for identifying polypeptides that bind yneS polypeptides, the conventional two-hybrid assays of protein/protein interactions can be used (see e.g., Chien et al., *Proc. Natl. Acad. Sci. USA,* 88:9578, 1991; Fields et al., U.S. Pat. No. 5,283,173; Fields and Song, *Nature,* 340:245, 1989; Le Douarin et al., *Nucleic Acids Research,* 23:876, 1995; Vidal et al., *Proc. Natl. Acad. Sci. USA,* 93:10315–10320, 1996; and White, *Proc. Natl. Acad. Sci. USA,* 93:10001–10003, 1996). Generally, the two-hybrid methods involve in vivo reconstitution of two separable domains of a transcription factor. One fusion protein contains a yneS polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the yneS polypeptide to the test polypeptide (i.e., candidate antibacterial agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate antibacterial (or anti-bacterial) agents. Having identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind yneS.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20%. Particularly potent test compounds may further reduce the growth rate (e.g., by at least 25%, 30%, 40%, 50%, 75%, 80%, or 90%).

Rodent (e.g., murine) and rabbit animal models of bacterial infections are known to those of skill in the art, and such animal model systems are accepted for screening antibacterial agents as an indication of their therapeutic efficacy in human patients. In a typical in vivo assay, an animal is infected with a pathogenic strain of bacteria, e.g., by inhalation of bacteria such as *Streptococcus pneumoniae,* and conventional methods and criteria are used to diagnose the mammal as being afflicted with a bacterial infection. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with the bacteria, and the ability of the treated mammal to resist infection is measured. Of course, the results obtained in the presence of the test compound should be compared with results in control animals, which are not treated with the test compound. Administration of candidate antibacterial agents to the mammal can be carried out as described below, for example.

Pharmaceutical Formulations

Treatment includes administering a pharmaceutically effective amount of a composition containing an antibacterial agent to a subject in need of such treatment, thereby inhibiting bacterial growth in the subject. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can be readily determined by those of ordinary skill in the art of medicine by monitoring the mammal for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject, and the condition of the subject to be treated. Generally, the antibacterial compound is administered at a dosage of 1 to 100 mg/kg of body weight, and typically at a dosage of 1 to 10 mg/kg of body weight.

Antibodies

The yneS polypeptide (or antigenic fragments or analogs thereof) can be used to raise antibodies useful in the invention, and such polypeptides can be produced by recombinant or peptide synthetic techniques (see, e.g., *Solid Phase Peptide Synthesis,* supra; Ausubel et al., supra). In general, the polypeptides can be coupled to a carrier protein, such as keyhole limpet hemocyanin (KLH), as described in Ausubel et al., supra, mixed with an adjuvant, and injected into a host mammal. A "carrier" is a substance that confers stability on, and/or aids or enhances the transport or immunogenicity of, an associated molecule. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, KLH, dinitrophenol, BCG (bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, F(ab')$_2$ fragments, and molecules produced using a Fab expression library.

Monoclonal antibodies (mAbs), which are homogeneous populations of antibodies to a particular antigen, can be prepared using a yneS polypeptide (or immunogenic fragment thereof) and standard hybridoma technology (see, e.g., Kohler et al., *Nature,* 256:495, 1975; Kohler et al., *Eur. J. Immunol.,* 6:511, 1976; Kohler et al., *Eur. J. Immunol.,* 6:292, 1976; Hammerling et al., In *Monoclonal Antibodies and T Cell Hybridomas,* Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature,* 256:495, 1975, and U.S. Pat. No. 4,376,110; the human B-cell hybridoma technique (Kosbor et al., *Immunology Today,* 4:72, 1983; Cole et al., *Proc. Natl. Acad. Sci. USA,* 80:2026, 1983); and the EBV-hybridoma technique (Cole et al., *Monoclonal Antibodies and Cancer Therapy,* Alan R. Liss, Inc., pp. 77–96, 1983). Such antibodies can be of any immunoglobulin class including IgG, IgM, IgE, IgA, IgD, and any subclass thereof. The hybridomas producing the mabs specific for yneS can be cultivated in vitro or in vivo.

Once produced, polyclonal or monoclonal antibodies are tested for specific recognition of a yneS polypeptide in an immunoassay, such as a Western blot or immunoprecipitation analysis using standard techniques, e.g., as described in Ausubel et al., supra. Antibodies that specifically bind to the yneS polypeptide, or conservative variants thereof, are useful in the invention.

Preferably, antibodies are produced using fragments of the yneS polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant yneS polypeptide, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; 4,946,778; and 4,704,692) can be adapted to produce single chain antibodies against a yneS polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind to a yneS polypeptide can be used, for example, to detect expression of a yneS gene in other bacteria. For example, a yneS polypeptide can be readily detected in conventional immunoassays of bacteria cells or extracts. Examples of suitable assays include, without limitation, Western blotting, ELISAs, radioimmune assays, and the like.

Other Embodiments

The methods of the invention also can be practiced with various fragments, variants, analogs, and derivatives of the yneS polypeptide described above that retain one or more of the biological activities of the yneS polypeptide. Naturally-occurring and non-naturally-occurring variants are useful in the invention. Compared with the naturally-occurring yneS gene sequences depicted in FIGS. 1 and 2, the nucleic acid sequences encoding variants may have a substitution, deletion, or addition of one or more nucleotides. The preferred variants retain a function of the yneS polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of bacterial growth also can be used with the yneS genes and gene products (including homologs and orthologs of the sequences disclosed herein).

What is claimed is:

1. A composition comprising a pharmaceutically acceptable excipient and a candidate antibacterial agent that specifically binds to an S-yneS polypeptide, wherein the antibacterial agent is an anti-streptococcal agent and is identified as a candidate antibacterial agent by a method comprising;

(a) contacting an S-yneS polypeptide with a test compound; and (b) detecting binding of the test compound with the S-yneS polypeptide, wherein binding indicates that the test compound is a candidate antibacterial agent.

2. A composition comprising a pharmaceutically acceptable excipient and an antibacterial agent that specifically binds to an S-yneS polypeptide, wherein the antibacterial agent is an anti-streptococcal agent and is identified by a method comprising:

(a) contacting an S-yneS polypeptide with a test compound;

(b) detecting binding of the test compound with the S-yneS polypeptide, wherein binding indicates that the test compound is a candidate to be an antibacterial agent; and (c) determining whether the candidate antibacterial agent inhibits growth of bacteria, relative to growth of bacteria cultured in the absence of the candidate antibacterial agent that binds with the polypeptide, wherein inhibition of growth indicates that the candidate antibacterial agent is an antibacterial agent.

3. The composition of claim 1, wherein the S-yneS polypeptide is a non-pathogenic *Streptococcus* polypeptide.

4. The composition of claim 1, wherein the S-yneS polypeptide is a pathogenic *Streptococcus* polypeptide.

5. The composition of claim 1, wherein the test compound is immobilized on a substrate, and binding of the test compound with the polypeptide is detected as immobilization of the polypeptide on the immobilized test compound.

6. The composition of claim 1, wherein the test compound is selected from the group consisting of polypeptides, ribonucleic acids, small molecules, and deoxyribonucleic acids.

7. The composition of claim 1, wherein:

the S-yneS polypeptide is provided as a fusion protein comprising the S-yneS polypeptide fused to (i) a transcription activation domain of a transcription factor or (ii) a DNA-binding domain of a transcription factor;

the test compound is a fusion protein comprising the polypeptide fused to (i) a transcription activation domain of a transcription factor or (ii) a DNA-binding domain of a transcription factor, to interact with the fusion protein; and binding of the test compound with the polypeptide is detected as reconstitution of a transcription factor.

8. The composition of claim 2, wherein the S-yneS polypeptide is a non-pathogenic *Streptococcus* polypeptide.

9. The composition of claim 2, wherein the S-yneS polypeptide is a pathogenic *Streptococcus* polypeptide.

10. The composition of claim 2, wherein the test compound is immobilized on a substrate, and binding of the test compound with the polypeptide is detected as immobilization of the polypeptide on the immobilized test compound.

11. The composition of claim 2, wherein the test compound is selected from the group consisting of polypeptides, ribonucleic acids, small molecules, and deoxyribonucleic acids.

12. The composition of claim 2, wherein:

the S-yneS polypeptide is provided as a fusion protein comprising the S-yneS polypeptide fused to (i) a transcription activation domain of a transcription factor or (ii) a DNA-binding domain of a transcription factor;

the test compound is a fusion protein comprising the polypeptide fused to (i) a transcription activation domain of a transcription factor or (ii) a DNA-binding domain of a transcription factor, to interact with the fusion protein; and binding of the test compound with the polypeptide is detected as reconstitution of a transcription factor.

* * * * *

SEQUENCE LISTING

<160> NUMBER OF SEQ ID NOS: 12

<210> SEQ ID NO 1
<211> LENGTH: 213
<212> TYPE: PRT
<213> ORGANISM: Streptococcus pneumoniae

<400> SEQUENCE: 1

```
Met Ile Thr Ile Val Leu Leu Ile Leu Ala Tyr Leu Leu Gly Ser Ile
 1               5                  10                  15

Pro Ser Gly Leu Trp Ile Gly Gln Val Phe Gln Ile Asn Leu Arg
            20                  25                  30

Glu His Gly Ser Gly Asn Thr Gly Thr Thr Asn Thr Phe Arg Ile Leu
        35                  40                  45

Gly Lys Lys Ala Gly Met Ala Thr Phe Val Ile Asp Phe Phe Lys Gly
    50                  55                  60

Thr Leu Ala Thr Leu Leu Pro Ile Ile Phe His Leu Gln Gly Val Ser
65                  70                  75                  80

Pro Leu Ile Phe Gly Leu Leu Ala Val Ile Gly His Thr Phe Pro Ile
                85                  90                  95

Phe Ala Gly Phe Lys Gly Gly Lys Ala Val Ala Thr Ser Ala Gly Val
            100                 105                 110

Ile Phe Gly Phe Ala Pro Ile Phe Cys Leu Tyr Leu Ala Ile Ile Phe
        115                 120                 125
```

```
Phe Gly Ala Leu Tyr Leu Gly Ser Met Ile Ser Leu Ser Ser Val Thr
            130                 135                 140

Ala Ser Ile Ala Ala Val Ile Gly Val Leu Leu Phe Pro Leu Phe Gly
145                 150                 155                 160

Phe Ile Leu Ser Asn Tyr Asp Ser Leu Phe Ile Ala Ile Ile Leu Ala
                165                 170                 175

Leu Ala Ser Leu Ile Ile Ile Arg His Lys Asp Asn Ile Ala Arg Ile
            180                 185                 190

Lys Asn Lys Thr Glu Asn Leu Val Pro Trp Gly Leu Asn Leu Thr His
        195                 200                 205

Gln Asp Pro Lys Lys
        210

<210> SEQ ID NO 2
<211> LENGTH: 642
<212> TYPE: DNA
<213> ORGANISM: Streptococcus pneumoniae
<220> FEATURE:
<221> NAME/KEY: CDS
<222> LOCATION: (1)...(639)

<400> SEQUENCE: 2 atg att aca ata gtt tta tta atc cta gcc tat ctg ctg ggt tcg att      48
Met Ile Thr Ile Val Leu Leu Ile Leu Ala Tyr Leu Leu Gly Ser Ile
  1               5                  10                  15 cca tct ggt ctc tgg att gga caa gta ttc ttt caa atc aat cta cgc      96
Pro Ser Gly Leu Trp Ile Gly Gln Val Phe Phe Gln Ile Asn Leu Arg
             20                  25                  30 gag cat ggt tct ggt aac act gga acg acc aac acc ttc cgc att tta     144
Glu His Gly Ser Gly Asn Thr Gly Thr Thr Asn Thr Phe Arg Ile Leu
         35                  40                  45 ggt aag aaa gct ggt atg gca acc ttt gtg att gac ttt ttc aaa gga     192
Gly Lys Lys Ala Gly Met Ala Thr Phe Val Ile Asp Phe Phe Lys Gly
     50                  55                  60 acc cta gca acg ctg ctt ccg att att ttt cat cta caa ggc gtt tct     240
Thr Leu Ala Thr Leu Leu Pro Ile Ile Phe His Leu Gln Gly Val Ser
 65                  70                  75                  80 cct ctc atc ttt gga ctt ttg gct gtt atc ggc cat acc ttc cct atc     288
Pro Leu Ile Phe Gly Leu Leu Ala Val Ile Gly His Thr Phe Pro Ile
                 85                  90                  95 ttt gca gga ttt aaa ggt ggt aag gct gtc gca acc agt gct gga gtg     336
Phe Ala Gly Phe Lys Gly Gly Lys Ala Val Ala Thr Ser Ala Gly Val
            100                 105                 110 att ttc gga ttt gcg cct atc ttc tgt ctc tac ctt gcg att atc ttc     384
Ile Phe Gly Phe Ala Pro Ile Phe Cys Leu Tyr Leu Ala Ile Ile Phe
        115                 120                 125 ttt gga gct ctc tat ctt ggc agt atg att tca ctg tct agt gtc aca     432
Phe Gly Ala Leu Tyr Leu Gly Ser Met Ile Ser Leu Ser Ser Val Thr
    130                 135                 140 gca tcg att gcg gct gtt atc ggg gtt ctg ctc ttt cca ctt ttt ggt     480
Ala Ser Ile Ala Ala Val Ile Gly Val Leu Leu Phe Pro Leu Phe Gly
145                 150                 155                 160 ttt atc ctg agt aac tat gac tct ctc ttc atc gct att atc tta gca     528
Phe Ile Leu Ser Asn Tyr Asp Ser Leu Phe Ile Ala Ile Ile Leu Ala
                165                 170                 175 ctt gct agt ttg att atc att cgt cat aag gac aat ata gct cgt atc     576
Leu Ala Ser Leu Ile Ile Ile Arg His Lys Asp Asn Ile Ala Arg Ile
            180                 185                 190 aaa aat aaa act gaa aat ttg gtc cct tgg gga ttg aac cta acc cat     624
```

```
Lys Asn Lys Thr Glu Asn Leu Val Pro Trp Gly Leu Asn Leu Thr His
        195                 200                 205 caa gat cct aaa aaa taa                                            642
Gln Asp Pro Lys Lys
        210

<210> SEQ ID NO 3
<211> LENGTH: 193
<212> TYPE: PRT
<213> ORGANISM: Streptococcus pneumoniae

<400> SEQUENCE: 3

Met Leu Ile Ala Leu Leu Ile Ile Leu Ala Tyr Leu Ile Gly Ser Ile
  1               5                  10                  15

Pro Ser Gly Leu Ile Val Gly Lys Leu Ala Lys Gly Ile Asp Ile Arg
             20                  25                  30

Glu His Gly Ser Gly Asn Leu Gly Ala Thr Asn Ala Phe Arg Thr Leu
         35                  40                  45

Gly Val Lys Ala Gly Ser Val Val Ile Ala Gly Asp Ile Leu Lys Gly
     50                  55                  60

Thr Leu Ala Thr Ala Leu Pro Phe Leu Met His Val Asp Ile His Pro
 65                  70                  75                  80

Leu Leu Ala Gly Val Phe Ala Val Leu Gly His Val Phe Pro Ile Phe
                 85                  90                  95

Ala Lys Phe Lys Gly Lys Ala Val Ala Thr Ser Gly Gly Val Leu
            100                 105                 110

Leu Phe Tyr Ala Pro Leu Leu Phe Ile Thr Met Val Ala Val Phe Phe
        115                 120                 125

Ile Phe Leu Tyr Leu Thr Lys Phe Val Ser Leu Ser Ser Met Leu Thr
130                 135                 140

Gly Ile Tyr Thr Val Ile Tyr Ser Phe Phe Val His Asp Thr Tyr Leu
145                 150                 155                 160

Leu Ile Val Val Thr Leu Leu Thr Ile Phe Val Ile Tyr Arg His Arg
                165                 170                 175

Ala Asn Ile Lys Arg Ile Ile Asn Lys Thr Glu Pro Lys Val Lys Trp
            180                 185                 190

Leu

<210> SEQ ID NO 4
<211> LENGTH: 582
<212> TYPE: DNA
<213> ORGANISM: Streptococcus pneumoniae
<220> FEATURE:
<221> NAME/KEY: CDS
<222> LOCATION: (1)...(579)

<400> SEQUENCE: 4 atg tta att gct tta ttg att att ttg gcc tac ttg ata ggc agc att    48
Met Leu Ile Ala Leu Leu Ile Ile Leu Ala Tyr Leu Ile Gly Ser Ile
  1               5                  10                  15 cca tct ggc tta att gtg ggc aag ctt gcc aaa gga att gat att cgg    96
Pro Ser Gly Leu Ile Val Gly Lys Leu Ala Lys Gly Ile Asp Ile Arg
             20                  25                  30 gag cac gga agc ggc aac tta ggc gct acc aat gca ttc cgt aca ttg   144
Glu His Gly Ser Gly Asn Leu Gly Ala Thr Asn Ala Phe Arg Thr Leu
         35                  40                  45 ggt gta aaa gct ggt tcg gtc gtc ata gcc gga gat att tgt aaa ggg   192
Gly Val Lys Ala Gly Ser Val Val Ile Ala Gly Asp Ile Leu Lys Gly
     50                  55                  60
```

```
aca ctg gca act gca ttg cct ttt ctc atg cat gtt gat att cac ccg      240
Thr Leu Ala Thr Ala Leu Pro Phe Leu Met His Val Asp Ile His Pro
 65                  70                  75                  80 ctt ctt gca gga gtc ttt gcg gtt tta ggc cac gtg ttt ccc atc ttc      288
Leu Leu Ala Gly Val Phe Ala Val Leu Gly His Val Phe Pro Ile Phe
                 85                  90                  95 gcc aaa ttt aaa ggc ggt aaa gcc gtg gcg aca tca gga ggc gtt ttg      336
Ala Lys Phe Lys Gly Gly Lys Ala Val Ala Thr Ser Gly Gly Val Leu
100                 105                 110 cta ttt tac gca ccc ctg tta ttt atc acg atg gtt gcg gta ttc ttc      384
Leu Phe Tyr Ala Pro Leu Leu Phe Ile Thr Met Val Ala Val Phe Phe
            115                 120                 125 atc ttt tta tac ttg act aaa ttt gtt tct ctc tca tcg atg tta aca      432
Ile Phe Leu Tyr Leu Thr Lys Phe Val Ser Leu Ser Ser Met Leu Thr
        130                 135                 140 ggg atc tat act gtt ata tat agt ttc ttt gtc cat gat acg tat tta      480
Gly Ile Tyr Thr Val Ile Tyr Ser Phe Phe Val His Asp Thr Tyr Leu
145                 150                 155                 160 ttg att gtc gtt acc ctg ctc act att ttt gtg ata tac aga cac cga      528
Leu Ile Val Val Thr Leu Leu Thr Ile Phe Val Ile Tyr Arg His Arg
                165                 170                 175 gcg aac att aaa cga att atc aat aaa aca gaa cct aaa gta aaa tgg      576
Ala Asn Ile Lys Arg Ile Ile Asn Lys Thr Glu Pro Lys Val Lys Trp
            180                 185                 190 tta taa                                                              582
Leu

<210> SEQ ID NO 5
<211> LENGTH: 21
<212> TYPE: DNA
<213> ORGANISM: B. subtilis

<400> SEQUENCE: 5
gtgttcgtgc tgacttgcac c                                              21

<210> SEQ ID NO 6
<211> LENGTH: 21
<212> TYPE: DNA
<213> ORGANISM: B. subtilis

<400> SEQUENCE: 6
gaattatttc ctcccgttaa a                                              21

<210> SEQ ID NO 7
<211> LENGTH: 21
<212> TYPE: DNA
<213> ORGANISM: Steptococcus pneumoniae

<400> SEQUENCE: 7
acccactccg tgaagtccac c                                              21

<210> SEQ ID NO 8
<211> LENGTH: 21
<212> TYPE: DNA
<213> ORGANISM: Streptococcus pneumoniae

<400> SEQUENCE: 8
gaacccagca gataggctag g                                              21

<210> SEQ ID NO 9
<211> LENGTH: 21
```

<212> TYPE: DNA
<213> ORGANISM: Steptococcus pneumoniae

<400> SEQUENCE: 9
gaacctaacc catcaagatc c                                            21

<210> SEQ ID NO 10
<211> LENGTH: 24
<212> TYPE: DNA
<213> ORGANISM: Streptococcus pneumoniae

<400> SEQUENCE: 10
cagttttaga tggctttaac agcg                                         24

<210> SEQ ID NO 11
<211> LENGTH: 642
<212> TYPE: DNA
<213> ORGANISM: Streptococcus pneumoniae

<400> SEQUENCE: 11
tactaatgtt atcaaaataa ttaggatcgg atagacgacc caagctaagg tagaccagag    60
acctaacctg ttcataagaa agtttagtta gatgcgctcg taccaagacc attgtgacct   120
tgctggttgt ggaaggcgta aaatccattc tttcgaccat accgttggaa acactaactg   180
aaaaagtttc cttgggatcg ttgcgacgaa ggctaataaa aagtagatgt tccgcaaaga   240
ggagagtaga aacctgaaaa ccgacaatag ccggtatgga agggatagaa acgtcctaaa   300
tttccaccat tccgacagcg ttggtcacga cctcactaaa agcctaaacg cggatagaag   360
acagagatgg aacgctaata gaagaaacct cgagagatag aaccgtcata ctaaagtgac   420
agatcacagt gtcgtagcta acgccgacaa tagccccaag acgagaaagg tgaaaaacca   480
aaataggact cattgatact gagagagaag tagcgataat agaatcgtga acgatcaaac   540
taatagtaag cagtattcct gttatatcga gcatagtttt tattttgact tttaaaccag   600 ggaacccta acttggattg ggtagttcta ggattttta tt                       642

<210> SEQ ID NO 12
<211> LENGTH: 582
<212> TYPE: DNA
<213> ORGANISM: Streptococcus pneumoniae

<400> SEQUENCE: 12
tacaattaac gaaataacta ataaaaccgg atgaactatc cgtcgtaagg tagaccgaat    60
taacacccgt tcgaacggtt tccttaacta taagccctcg tgccttcgcc gttgaatccg   120
cgatggttac gtaaggcatg taacccacat tttcgaccaa gccagcagta tcggcctcta   180
taaaactttc cctgtgaccg ttgacgtaac ggaaaagagt acgtacaact ataagtgggc   240
gaagaacgtc ctcagaaacg ccaaaatccg gtgcacaaag ggtagaagcg gtttaaattt   300
ccgccatttc ggcaccgctg tagtcctccg caaaacgata aaatgcgtgg ggacaataaa   360
tagtgctacc aacgccataa gaagtagaaa aatatgaact gatttaaaca agagagagt   420 agctacaatt gtccctagat atgacaatat atatcaaaga aacaggtact atgcataaat   480
aactaacagc aatgggacga gtgataaaaa cactatatgt ctgtggctcg cttgtaattt   540
gcttaatagt tattttgtct tggatttcat tttaccaata tt                     582